United States Patent [19]
Samuels

[11] Patent Number: 5,908,435
[45] Date of Patent: Jun. 1, 1999

[54] EXPANDABLE LUMEN DEVICE AND METHOD OF USE

[76] Inventor: Shaun L. W. Samuels, 1055 Sonoma Ave., Menlo Park, Calif. 94025

[21] Appl. No.: 08/956,951

[22] Filed: Oct. 23, 1997

[51] Int. Cl.$^6$ .................................................... A61M 29/00
[52] U.S. Cl. ............................................ 606/200; 606/127
[58] Field of Search ..................................... 606/200, 127, 606/128, 194, 191

[56] References Cited

U.S. PATENT DOCUMENTS

| | | |
|---|---|---|
| 4,531,943 | 7/1985 | Van Tassel et al. . |
| 4,873,978 | 10/1989 | Ginsburg .................................. 606/200 |
| 4,927,426 | 5/1990 | Dretler . |
| 5,092,839 | 3/1992 | Kipperman . |
| 5,234,425 | 8/1993 | Fogarty et al. . |
| 5,256,150 | 10/1993 | Quiachon et al. . |
| 5,312,417 | 5/1994 | Wilk .......................................... 606/127 |
| 5,423,851 | 6/1995 | Samuels . |
| 5,549,626 | 8/1996 | Miller et al. ............................. 606/200 |
| 5,707,359 | 1/1998 | Bufalini ................................... 606/200 |

*Primary Examiner*—Michael Buiz
*Assistant Examiner*—Kevin Truong
*Attorney, Agent, or Firm*—Rudnick & Wolfe; William T. Rifkin; R. Blake Johnston

[57] ABSTRACT

A device for removing undesirable material from a tubular structure within the human body features a cylindrical body with a lumen therethrough. The distal portion of the body is divided into a number of flexible members. An inflatable cuff is attached to the flexible members. When the cuff is inflated, the members flex radially outwardly so that the distal opening of the lumen is expanded. An inflation tube is used to inflate and deflate the cuff by means of a syringe. An elastomeric membrane sleeve surrounds the flexible members so that the latter are contracted towards their original position when the cuff is deflated. The sleeve also prevents material from escaping between the flexible members when the cuff is inflated.

15 Claims, 3 Drawing Sheets

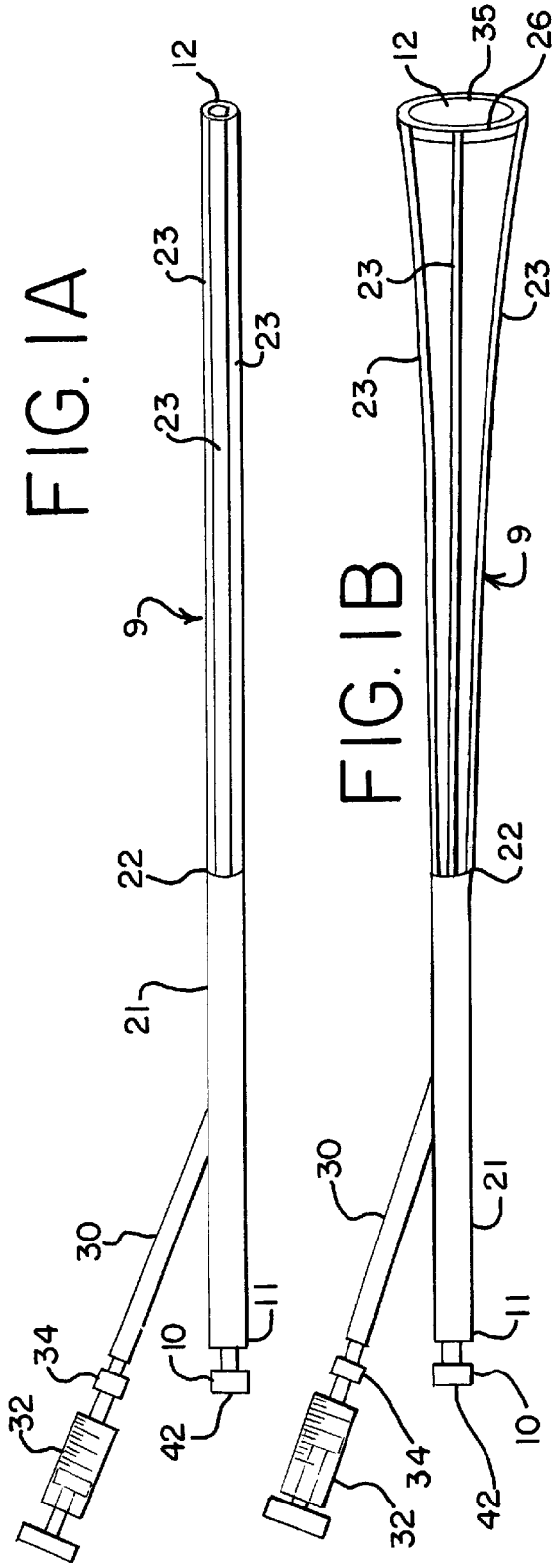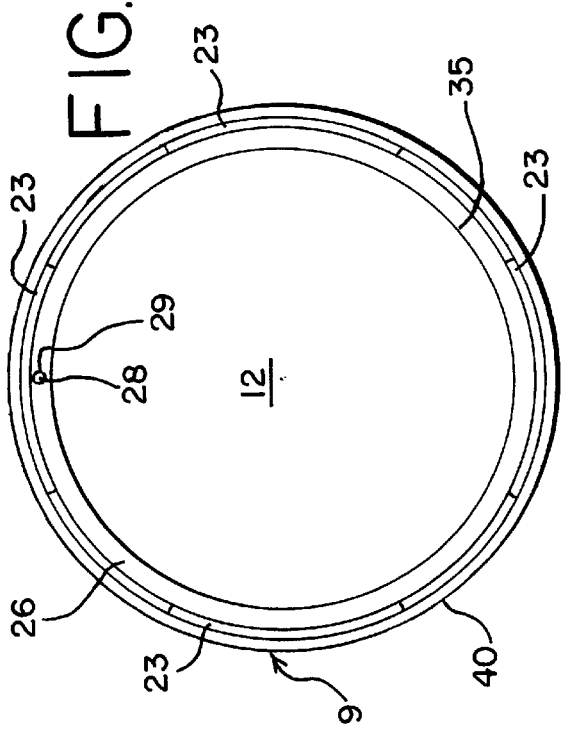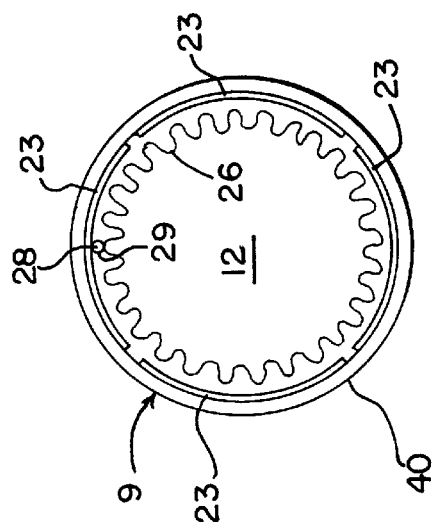

EXPANDABLE LUMEN DEVICE AND METHOD OF USE

BACKGROUND

Various tubular structures within the human body may come to contain materials, whether of the body's origin or man-made, that are undesirable. For example, stones may develop in the biliary or excretory systems, blood clots may form in blood vessels, or surgically implanted devices, such as catheters, may have fragments break off. For most of these situations, surgical intervention has traditionally been the primary means of retrieval and treatment.

Recently, however, various interventional radiological techniques have been developed which allow removal of such undesirable material. Such techniques involve the introduction of guide wires and catheters, or other medical devices, into the lumen of the tubular structures through introducer sheaths.

In one type of interventional radiological technique, various baskets, such as the SEGURA basket, manufactured by the Meditech corporation of Watertown, Mass., are used for trapping stones in the biliary and excretory tracts. Unfortunately, such devices are not easily inserted into, or manipulated within, the lumen of a human body's tubular structures. The baskets also generally contain wire mesh that may damage the interior walls of tubular structures.

Interventional radiologic techniques have been developed in which pharmacologic agents, such as urokinase, are used through catheter directed infusion to dissolve blood clots. This dissolving of clots is a relatively lengthy process and is extremely expensive. Furthermore, the process poses significant risks to the patient, the most serious of these being the precipitation of bleeding elsewhere in the body.

In U.S. Pat. No. 4,927,426 to Dretler, there is disclosed a device for capturing and disintegrating kidney stones and the like. The device features a snare that passes through the lumen of a catheter. Once the catheter is positioned within a passage of the human body, such as the urinary tract, the snare may be extended out of the catheter's distal end in an axial direction so that it may capture a kidney stone. The catheter has an elastomeric structure on its distal end which is inverted on itself as the kidney stone is drawn axially into the lumen of the catheter. The snare features an elongated tube through which a laser fiber passes. This allows the kidney stone to be disintegrated as it is held within the catheter. A disadvantage of this device, however, is that it features a profile that would preclude introduction into the vascular system. Furthermore, the elastomeric structure on the distal end of the catheter has undesirable consequences, as will be discussed below.

U.S. Pat. No. 5,092,839 to Kipperman discloses a method and apparatus for removing thrombus and plaque from a coronary artery. The apparatus features a balloon catheter disposed through the lumen of a guide catheter. The guide catheter features an expandable distal tip. Once the device is positioned within the artery, the balloon is inflated to expand the distal tip of the guide catheter. The balloon is then deflated and the distal tip of the guide catheter retains its expanded shape. The balloon catheter is then extended out from the distal tip and beyond the occluded portion of the artery and is once again inflated. The inflated balloon is then retracted back into the guide catheter, carrying with it residual pieces of thrombus and/or plaque which had been dislodged from the artery wall. A disadvantage of this apparatus and method, however, is that, in order to properly expand the distal tip of the guide catheter, the balloon must be precisely positioned. Furthermore, once the distal tip is expanded, it cannot be contracted. This would make removal from the patient's body or advancement further into the artery difficult if not impossible.

In order to accommodate the retrieval and removal of foreign bodies that are larger than the inner diameter of their distal tips, a number of sheaths and catheters have been constructed from elastomeric substances. An example is the EVC catheter available from the Applied Medical corporation of Laguna Beach, Calif. A disadvantage of existing elastomeric sheaths and catheters, however, is that, because of their elastomeric construction, they are easily deformed in an accordion-like fashion when an object is brought up forcefully against their orifices. Furthermore, due to their deformability, such sheaths and catheters may be peeled back during introduction through the skin or while entering the target structure. This could render the device useless and may possibly result in damage to the skin or target structure.

Accordingly, it is an object of the present invention to provide a catheter, which may be in the form of a typical catheter, a guide catheter or an introducer sheath, and a method of use by which a variety of undesirable materials may be removed from tubular structures within the human body.

It is also an object of the present invention to provide a catheter with a lumen which may be easily expanded once the catheter is introduced into a tubular structure of the human body so as to allow for passage of materials into the tip of the catheter for easier removal from the body.

It is a further object of the present invention to provide a catheter with an expandable lumen that is elastic so that it may be contracted back to its original size while in a tubular structure in the human body.

It is a further object of the present invention to provide a catheter which allows for elastic expansion of its lumen while maintaining adequate longitudinal strength to resist accordion-like deformation.

It is still a further object of the present invention to provide a catheter which allows for elastic expansion of its lumen and may be easily introduced and withdrawn from a tubular structure of the human body.

SUMMARY

The present invention is directed to an expandable lumen device for retrieving material from tubular structures within the human body. The device is particularly useful for retrieving material that normally would be too large for the opening of a typical catheter or sheath. The device may take the form of a catheter, sheath or the like. It features a cylindrical body defining a central lumen with a distal opening. The proximal portion of the body features a solid wall while the wall of the distal portion is divided into a plurality of flexible members.

An inflatable cuff is attached to the interior surfaces of the flexible members near the distal opening of the lumen. As a result, when the cuff is inflated, the flexible members move radially outwardly so as to expand the distal opening of the lumen so that relatively large materials may be retrieved into the lumen. An elastic sleeve surrounds the flexible members so that they are drawn together when the cuff is deflated. The elastic sleeve also prevents the escape of material between the flexible members when the cuff is inflated.

A cuff inflation tube is in fluid communication with the inflatable cuff and is secured to the interior surface of one of the flexible members and runs longitudinally through the central lumen. The proximal end of the cuff inflation tube is in communication with a side port which in turn is in communication with a syringe. Manipulation of the syringe causes the cuff to inflate.

In use, a guide wire is introduced into a tubular structure of the human body. Next, the device, with a central dilator in its lumen, is guided via the guide wire through the tubular structure to the location of the material to be removed. Once the device is in position, the central dilator is removed. The cuff is then inflated so as to enlarge the distal opening of the lumen to a size that is compatible with the material. A balloon catheter or snare is then fed through the lumen and is used to push or pull the material into the cental lumen of the device. Once the material is captured within the device, the cuff is deflated so that the distal opening of the lumen contracts. The material may then be removed from the tubular structure through the central lumen or the entire device itself may be removed with the material captured inside.

For a more complete understanding of the nature and scope of the invention, reference may now be had to the following detailed description of embodiments thereof taken in conjunction with the appended claims and accompanying drawings.

BRIEF DESCRIPTION OF THE DRAWINGS

FIGS. 1A and 1B show perspective partial sectional views of a catheter that is an embodiment of the present invention with its cuff in deflated and inflated states, respectively;

FIGS. 2A and 2B show end axial views of the distal end of the catheter of FIGS. 1A and 1B, respectively;

DESCRIPTION

Figure 3A:
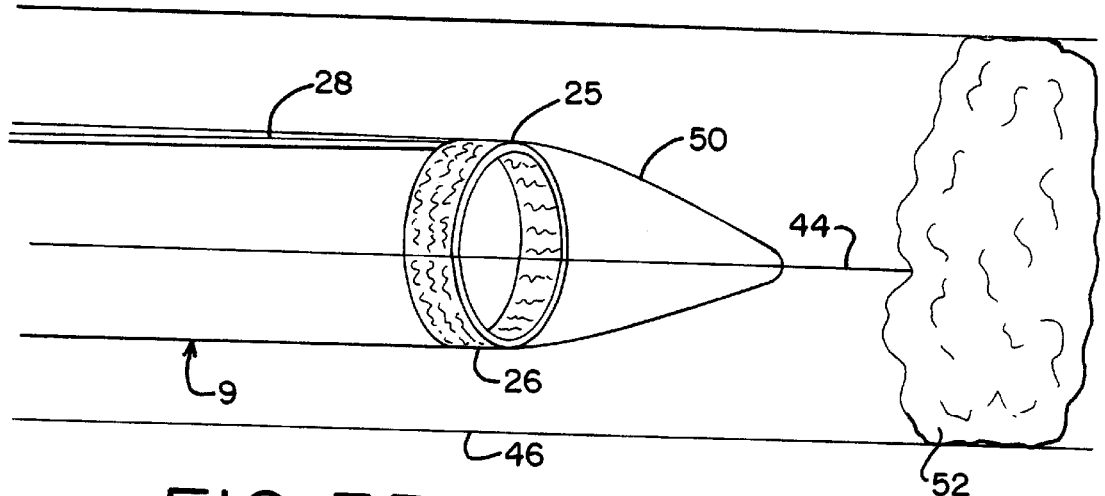
FIGS. 3A through 3E show partial sectional perspective views of the catheter of FIGS. 1A and 1B being used in accordance with the method of the present invention to remove a blood clot from a blood vessel.

Referring to FIGS. 1 and 2, a catheter that is an embodiment of the present invention is shown. It is to be understood that embodiments of the invention may take the form of a typical catheter, a guide catheter, an introducer sheath or the like. Catheter cylindrical body 9 features Luer Lock hub 10 mounted on its proximal end 11 and a central lumen 12 through which a guide wire and other devices may be passed. The proximal portion 21 of catheter body 9 is fixed so as to provide rigidity. Catheter body 9 is preferably constructed of either a plastic polymer or a metallic substance. At junction point 22, the catheter body 9 divides into flexible members 23 that, in their unexpanded state, as shown in FIG. 1A, maintain the same cylindrical shape as proximal portion 21 over the remaining length of the catheter body 9. The distal portion of catheter body 9 may involve as few as two and as many as eight flexible members 23. The flexible members 23 provide a measure of rigidity to the distal portion of the catheter body while at the same time allowing radial expansion.

Distal tip 25 features an inflatable cuff 26 attached about the circumference of the interior surface of members 23. Cuff 26 may be attached by bonding using biologically inert adhesives or a loop formed in the material of the flexible members 23. Cuff 26 is preferably composed of a slightly elastic plastic polymer which is biologically inert and expands to a predictable degree under inflation pressure. Plastics such as polyurethane may be used for this purpose. The walls of inflatable cuff 26 are thin, so as to minimize added thickness to the profile of lumen 12.

A cuff inflation tube 28 provides a dedicated inflation lumen 29 that is in fluid communication with cuff 26. Cuff inflation tube 28 is connected to the interior surface of one of the members 23 so as to run longitudinally through lumen 12. A side port 30 is connected to the proximal portion 21 of catheter body 9 and communicates with the proximal end of cuff inflation tube 28. A syringe 32 connects to side port 30 via a Luer Lock hub 34. Inflation of cuff 26 is accomplished by the injection of fluid, most appropriately one containing a radiopaque contrast, through cuff inflation tube 28 via syringe 23. The inflation of cuff 26 with liquid containing radiopaque contrast allows for easier positioning of the catheter during an interventional radiological procedure.

In FIGS. 1B and 2B, catheter body 9 is shown with the distal end of the lumen opening 35 in an expanded state. The diameter of expanded opening 35 is chosen depending upon the size of the tubular structure of the human body within which the catheter is placed. Opening 35 maybe expanded with the intent of engaging the interior of the wall of the tubular structure so as to create a circumferential occlusive seal therein. However, in situations in which flow through the tubular structure cannot be completely interrupted, as, for example, in a main artery, the expanded diameter may be chosen so as to create an enlarged orifice, but without circumferential contact with the interior of the wall of the tubular structure. Flow may then continue around opening 35.

As shown in FIGS. 2A and 2B, encircling the entirety of catheter body 9 is an elastomeric membrane sleeve 40 (omitted for clarity in FIGS. 1A and 1B), affixed to the outer surface of the catheter body members 23. The elastomeric membrane sleeve 40 serves two main purposes. First, the membrane, by its elastic nature, contracts the members 23 so that the distal portion of catheter body 9 resumes its original shape after cuff 26 has been deflated. Secondly, since inflation of cuff 26 forces the flexible members 23 away from one another, thus creating substantial space between them, the ability of the catheter to accept and trap material is compromised in the absence of a membrane which spans these members. Elastic membrane sleeve 40 thus maintains a continuous wall about lumen 12 through which material drawn thereinto may pass to the exit port 42.

FIGS. 3A through 3E show the catheter being used in accordance with the method of the invention to remove a blood clot from a vessel. It is to be understood that use of the device in a blood vessel to remove a blood clot is presented as an example only and that the catheter and method of the present invention may be used to remove a variety of undesirable materials from a number of different tubular structures in the human body. The latter includes, but is not limited to, tubular structures of the biliary, excretory and vascular systems.

Figure 3B:
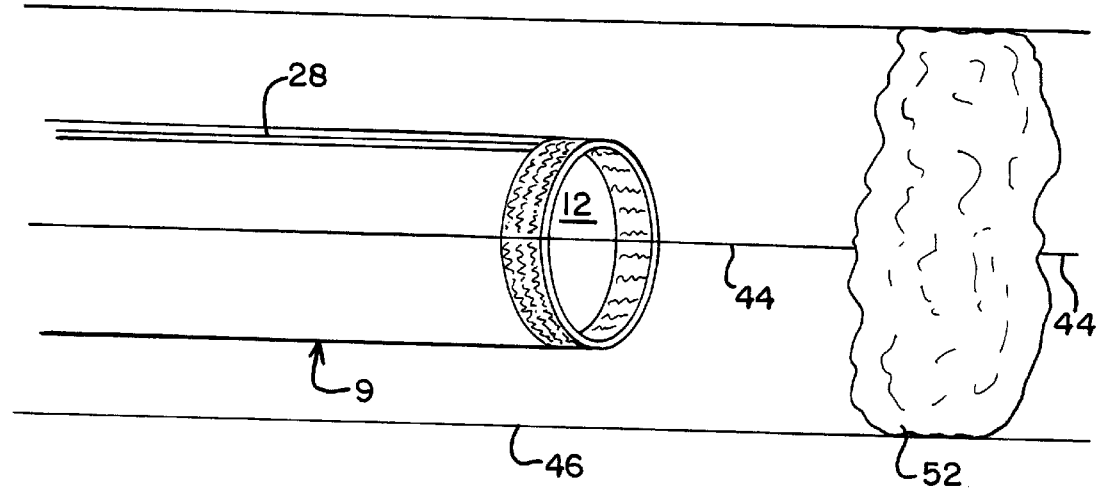

As shown in FIG. 3A, a guide wire 44 has been inserted into the blood vessel 46. Next, catheter body 9 is introduced into blood vessel 46 with a central dilator 50 disposed ahead of the catheter. This is done so that the blunt end 25 of the catheter body 9 does not damage the walls of vessel 46 as it is advanced. During this stage, cuff 26 is deflated. Catheter body 9 is guided to the location of a blood clot 52 via travel along guide wire 44 (which, it is noted, passes through the clot). Once the catheter body 9 is in the proper position, as shown in FIG. 3B, central dilator 50 is removed. At this point, catheter body 9 may be partially withdrawn if desired. However, it should never be advanced without central dilator 50 in place for the reason mentioned above.

Figure 3C:
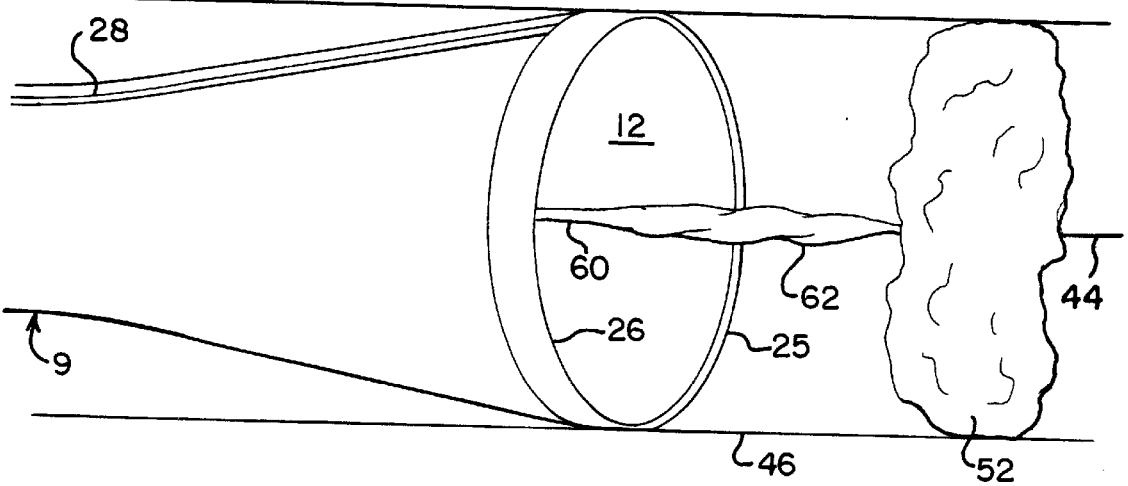

Next, as shown in FIG. 3C, cuff 26 is inflated so that the distal end 25 of catheter body 9 is able to accommodate clot 52. A balloon catheter 60 is then passed, in a deflated condition, along guide wire 44, through lumen 12 and through clot 52. Such balloon catheters are well known in the art.

Figure 3D:
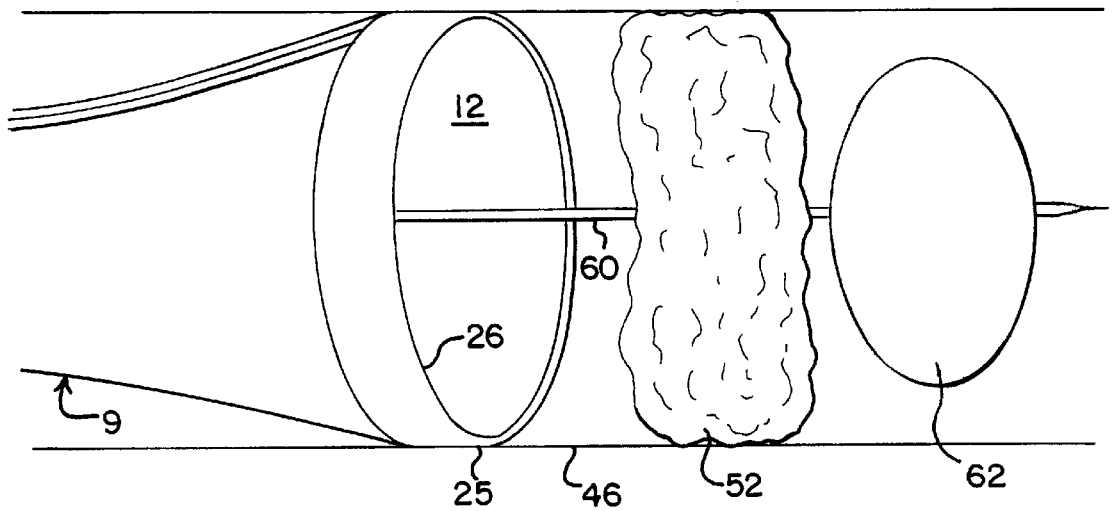
Figure 3E:
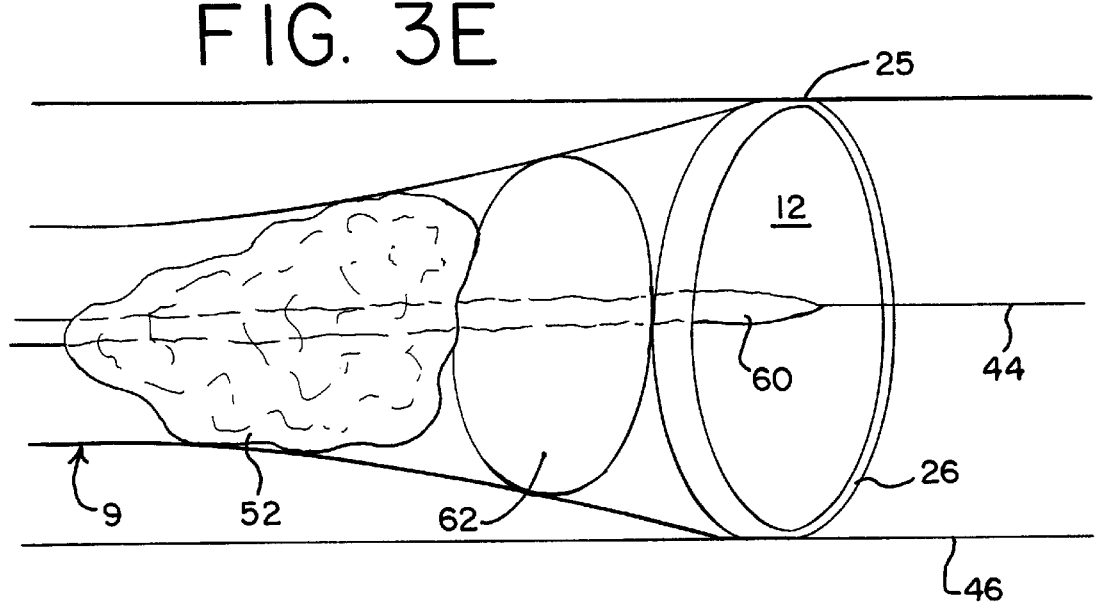

Referring to FIG. 3D, once the balloon portion 62 of balloon catheter 60 has passed through clot 52, it is inflated via methods well known in the art. After the balloon portion 62 is inflated, as shown in FIG. 3E, the clot is pulled into catheter body 9 with expanded distal end 25 providing proper clearance. With clot 52 captured within catheter body 9, cuff 26 is deflated so that the distal end 25 contracts back towards its original size and shape. This results in clot 52 being compacted by the interior surfaces of members 23 as they are pulled radially inwards by elastomeric membrane sleeve 40. During this stage, the balloon portion 62 of balloon catheter 60 is also permitted to deflate. With distal tip 25 contracted back to approximately its original size and shape, and clot 52 compacted within the catheter body 9, the unit may be easily removed from the vessel of the patient. Alternatively, the balloon catheter 60 may be used to pull clot 52 through the remaining portion of catheter body 9, including proximal end 21, through lumen 12 and out exit port 42 (see FIGS. 1A and 1B). In this manner, clots are removed from the vessel and body without necessitating reinsertion of catheter body 9 should retrieval of additional clots be desirable.

While a balloon catheter 60 has been used in the example presented in FIGS. 3A through 3E, a snare or other retrieving device may be used as an alternative. This would be necessary, for example, in situations wherein the undesirable material to be removed is not penetrable.

While the preferred embodiments of the invention have been shown and described, it will be apparent to those skilled in the art that changes and modifications may be made therein without departing from the spirit of the invention, the scope of which is defined by the appended claims.

What is claimed is:

1. A device for retrieving material from tubular structures within the human body comprising:
    a) a cylindrical body defining a central lumen, the cylindrical body having a proximal portion and a distal portion, said distal portion being radially expandable and having an end with an opening;
    b) an inflatable cuff attached to said end of said distal portion, said cuff when inflated causing the distal portion to move radially outward to expand the diameter of the opening in the end of the distal portion;
    c) an inflation lumen in fluid communication with said inflatable cuff; and
    d) means for inflating and deflating said inflatable cuff through said inflation lumen.

2. The device of claim 1 wherein said distal portion of the cylindrical body includes a surface to which said inflatable cuff is attached.

3. The device of claim 2 wherein said inflation lumen is a cuff inflation tube.

4. The device of claim 3 wherein said cuff inflation tube is attached to the surface of the distal portion of the cylindrical body.

5. The device of claim 1 wherein said means for inflating and deflating said inflatable cuff includes a side port formed in the proximal portion of said cylindrical body and in communication with said inflation lumen.

6. The device of claim 5 wherein said means for inflating and deflating said inflatable cuff includes a syringe in communication with said side port.

7. The device of claim 1 wherein said distal portion includes a plurality of flexible members, said flexible members moving radially outwards so as to expand the opening of the end of the distal portion when said inflatable cuff is inflated.

8. The device of claim 7 wherein said plurality of flexible members are surrounded by an elastomeric membrane sleeve so that the members are drawn together when said inflatable cuff is deflated.

9. An expandable lumen device for retrieving matter from tubular structures within the human body comprising:
    a) a cylindrical body defining a central lumen with a distal opening, the cylindrical body having a proximal portion and a distal portion with said distal portion defined by a plurality of flexible members;
    b) an inflatable cuff attached to said plurality of flexible members so that when said inflatable cuff is inflated, the flexible members move radially outwardly so as to expand the distal opening of the central lumen;
    c) an elastomeric membrane sleeve surrounding the plurality of flexible members so that said plurality of flexible members are drawn together when said inflatable cuff is deflated;
    d) an inflation lumen in fluid communication with said inflatable cuff; and
    e) means for inflating and deflating said inflatable cuff through the inflation lumen.

10. The expandable lumen device of claim 9 wherein said flexible members include surfaces to which said inflatable cuff is attached.

11. The expandable lumen device of claim 10 wherein the inflation lumen is a cuff inflation tube.

12. The expandable lumen device of claim 11 wherein said cuff inflation tube is attached to the surface of one of the flexible members.

13. The expandable lumen device of claim 9 wherein said means for inflating and deflating said inflatable cuff includes a side port formed in the proximal portion of said cylindrical body and in communication with said inflation lumen.

14. The expandable lumen device of claim 13 wherein said means for inflating and deflating said inflatable cuff includes a syringe in communication with said side port.

15. The expandable lumen device of claim 9 further comprising an exit port formed in the proximal portion of said cylindrical body and in communication with said central lumen.

* * * * *